United States Patent
Nakazono et al.

(10) Patent No.: US 8,911,838 B2
(45) Date of Patent: Dec. 16, 2014

(54) OPTICAL FILM MATERIAL ROLL AND METHOD FOR MANUFACTURING IMAGE DISPLAY DEVICE USING THEREOF

(75) Inventors: Takuya Nakazono, Ibaraki (JP); Seiji Umemoto, Ibaraki (JP); Tomohito Takita, Ibaraki (JP); Fumihito Shimanoe, Ibaraki (JP); Yuuki Yano, Ibaraki (JP); Teruaki Oosawa, Ibaraki (JP)

(73) Assignee: Nitto Denko Corporation, Ibaraki-shi (JP)

( * ) Notice: Subject to any disclaimer, the term of this patent is extended or adjusted under 35 U.S.C. 154(b) by 0 days.

(21) Appl. No.: 13/058,278

(22) PCT Filed: Apr. 1, 2010

(86) PCT No.: PCT/JP2010/055999
§ 371 (c)(1),
(2), (4) Date: Feb. 9, 2011

(87) PCT Pub. No.: WO2010/116944
PCT Pub. Date: Oct. 14, 2010

(65) Prior Publication Data
US 2011/0143056 A1    Jun. 16, 2011

(30) Foreign Application Priority Data

Apr. 10, 2009 (JP) ................................ 2009-096277
Mar. 9, 2010 (JP) ................................ 2010-052036

(51) Int. Cl.
*C09K 19/00* (2006.01)
*G02B 5/30* (2006.01)
*B32B 41/00* (2006.01)
*G01N 21/88* (2006.01)

(52) U.S. Cl.
CPC .............. *G02B 5/3041* (2013.01); *B32B 41/00* (2013.01); *B32B 2041/04* (2013.01); *B32B 2457/202* (2013.01); *G01N 2021/888* (2013.01)

USPC .......... 428/1.3; 428/1.31; 428/1.33; 156/263; 264/1.34; 349/96

(58) Field of Classification Search
USPC ............ 428/1.3, 1.31, 1.33; 156/263; 349/96; 264/1.34
See application file for complete search history.

(56) References Cited

U.S. PATENT DOCUMENTS 6,309,118 B1    10/2001 Konno et al.
6,342,096 B1 *    1/2002 Kurabayashi ............... 106/31.27
(Continued)

FOREIGN PATENT DOCUMENTS

JP      4-008586 A    1/1992
JP      09-304295 A   11/1997
(Continued)

OTHER PUBLICATIONS

Mechine translation of JP 2003-139713A and 2005-062165A.*
(Continued)

*Primary Examiner* — Michele L Jacobson
*Assistant Examiner* — Ruiyun Zhang
(74) *Attorney, Agent, or Firm* — Westerman, Hattori, Daniels & Adrian, LLP

(57) ABSTRACT

Disclosed is a material roll that includes a roll of an optical film having defect information markings printed thereon and is resistant to the formation of a defect by the transfer of a bump/dent deformation at the marking site. The material roll includes a long sheet of an optical film with polarizer wound into roll shape; and marking(s) formed at or in a vicinity of at least one defect site. The marking has an optical density of 1.5 or more, and a thickness of a center part of the marking is 1.5 μm or less. The marking preferably has an optical density per unit thickness of 2.5 μm$^{-1}$ or more.

3 Claims, 3 Drawing Sheets

(56) References Cited

U.S. PATENT DOCUMENTS

| | | |
|---|---|---|
| 2002/0139273 A1 | 10/2002 | Murata et al. |
| 2004/0046858 A1* | 3/2004 | Yoshinari .................... 347/213 |
| 2005/0232475 A1 | 10/2005 | Floeder et al. |
| 2006/0164647 A1* | 7/2006 | Shibata ........................ 356/430 |
| 2008/0193701 A1 | 8/2008 | Takayanagi et al. |
| 2009/0199950 A1 | 8/2009 | Kitada et al. |
| 2010/0040278 A1 | 2/2010 | Floeder et al. |
| 2010/0165333 A1 | 7/2010 | Ohashi et al. |
| 2010/0288441 A1 | 11/2010 | Kitada et al. |
| 2011/0211747 A1 | 9/2011 | Floeder et al. |

FOREIGN PATENT DOCUMENTS

| | | |
|---|---|---|
| JP | 9-304295 A | 11/1997 |
| JP | 10-268136 A | 10/1998 |
| JP | 2000-009659 A | 1/2000 |
| JP | 2001-080183 A | 3/2001 |
| JP | 2002-292853 A | 10/2002 |
| JP | 2003-014934 A | 1/2003 |
| JP | 2003-139713 A | 5/2003 |
| JP | 2004-045071 A | 2/2004 |
| JP | 2004-195713 A | 7/2004 |
| JP | 2005-062165 A | 3/2005 |
| JP | 2006-038778 A | 2/2006 |
| JP | 2006-290535 A | 10/2006 |
| JP | 2006-327069 A | 12/2006 |
| JP | 2006-347007 A | 12/2006 |
| JP | 2007-076106 A | 3/2007 |
| JP | 2007-114139 A | 5/2007 |
| JP | 3974400 B2 | 9/2007 |
| JP | 2008-032747 A | 2/2008 |
| JP | 2008-197159 A | 8/2008 |
| JP | 2009-061744 A | 3/2009 |
| JP | 2009-69142 A | 4/2009 |
| TW | 200602614 A | 1/2006 |
| WO | 2008/047712 A1 | 4/2008 |

OTHER PUBLICATIONS

International Search Report of PCT/JP2010/055999, date of mailing Apr. 27, 2010.
Japanese Office Action dated Jan. 6, 2011, issued in corresponding Japanese Patent Application No. 2010-27417.
Japanese Office Action dated Jul. 29, 2010, issued in corresponding Japanese Patent Application No. 2010-05236.
Decision of Appeal dated May 10, 2011, issued in corresponding Japanese Patent Application No. 2010-052036. (Appeal No. 2010-27417).
Notification of Transmittal of Translation of the International Preliminary Report on Patentability (Form PCT/IB/338) of International Application No. PCT/JP2010/055999 mailed Nov. 24, 2011 with forms PCT/IB/373 and PCT/ISA/237.
Taiwanese Office Action dated Oct. 20, 2011, issued in corresponding Taiwanese Patent Application No. 099110769.
Chinese Office Action mailed Apr. 5, 2012, issued in corresponding Chinese Patent Application No. 201080002197.2, with English translation (8 pages).
Chinese Office Action dated Oct. 31, 2012, issued in corresponding Chinese Patent Application No. 201080002197.2, with English translation (9 pages).
European Search Report dated May 30, 2012, issued in corresponding European Patent Application No. 10761643.5, (6 pages).
U.S. Non-Final Office Action dated Jan. 31, 2014, issued in corresponding U.S. Appl. No. 13/447,963.
The Decision of Rejection dated Dec. 3, 2013 in corresponding Chinese Application No. 201080002197.2 w/ English Translation. (8 pages).
European Search Report dated Sep. 17, 2012, issued in corresponding European patent application 10761643.5.
Chinese Office Action dated May 23, 2013, issued in corresponding Chinese Patent Application No. 201080002197.2, w/ English translation.

* cited by examiner

OPTICAL FILM MATERIAL ROLL AND METHOD FOR MANUFACTURING IMAGE DISPLAY DEVICE USING THEREOF

TECHNICAL FIELD

The invention relates to a material roll of a long sheet of an optical film including a polarizer, which has marking(s) at or in a vicinity of defect sites. The invention also relates to a method for manufacturing an image display device such as a liquid crystal display by bonding a piece from the material roll to an optical display unit such as a liquid crystal cell.

BACKGROUND ART

In recent years, as the screen size of liquid crystal televisions, etc. has increased, more stringent demands have been placed on the display properties of optical films such as polarizing plates for use in image display devices such as liquid crystal displays, and more strict control of optical defects has been demanded. To meet these demands, there have been used methods of detecting optical defects with human eyes or automatic inspection apparatuses and removing them. When defects are detected, the information about their positions can be recorded, and the parts including defects can be eliminated so as not to be bonded to an optical display unit, so that an image display device as an end product can be prevented from being contaminated with optical film-derived defects. This can reduce the optical film loss and the rate at which reworking has to be performed to peel off the defective optical film from the optical display unit and therefore can contribute to an increase in yield and cost savings.

Proposed methods for recording positional information about detected defects include a method of printing a marking at a defect site generally with ink or the like (see for example Patent Document 1), a method of printing, on a film, bar code information or coded character information about the result of detection of defects (see for example Patent Document 2), and a method of attaching a recorded media such as an IC chip to an optical film product (see for example Patent Document 3).

When printing on an optical film is performed as described in Patent Document 1 or 2, the printed site has an increased thickness due to the thickness of the ink or the like used to form the marking, although the increase in thickness is very small. Therefore, the process of winding the optical film into a roll may cause a problem in which the thickness difference at the printed site, specifically a bump/dent deformation is transferred to a part in contact with the printed site, so that a new deformation such as a dent can occur to form a new defect in an originally-non-defective part. To prevent such transfer-induced defects, there is proposed a method of printing on a transverse end of an optical film outside the effective width of the optical film, specifically on a part not to be bonded to an optical display unit such as a liquid crystal cell (see for example Patent Document 4).

In addition to the demands for defect reduction, demands for reductions in the cost of image display devices are increasing every year. To meet the demands, there is proposed a method of manufacturing an image display device using a continuous manufacturing line that includes feeding means for feeding a long optical film from a roll of the long optical film, cutting means for cutting the optical film at specific intervals along the feed direction, and bonding means for bonding the cut piece of the optical film to an optical display unit (see Patent Document 5). Such a system makes it possible to directly cut the optical film from the material roll into the desired size and to directly bond the cut piece of the optical film to the optical display unit. Therefore, such a system makes it possible to directly package the material roll and to deliver it and therefore can contribute to a reduction in the number of man-hours or process materials, in contrast to a conventional method including stamping a sheet material of an optical film into pieces of the desired size, carefully packaging each piece of the optical film after the stamping, and delivering it to a panel processing manufacturer.

If the manufacturing method disclosed in Patent Document 5 is controlled in such a manner that the optical film is inspected for defects before it is cut by the cutting means and that defective parts of the optical film are not bonded to the optical display unit, the yield of the end product, an image display device, can be increased.

Patent Document 5 proposes that in the defect inspection, the optical film should be inspected for defects after a release film (separator) is temporarily peeled off from the optical film, and then a separator should be attached to the optical film again. Alternatively, detect inspection may be performed in advance, and the resulting defect information may be recorded on the material roll as described in Patent Documents 1 to 4, so that the optical film from the material roll can be directly cut into the desired size without peeling off the separator and that the cut piece of the optical film can be directly bonded to the optical display unit.

PRIOR ART DOCUMENTS

Patent Documents

Patent Document 1: Japanese Patent Application Laid-Open (JP-A) No. 09-304295
Patent Document 2: Japanese Patent No. 3974400
Patent Document 3: JP-A No. 2008-32747
Patent Document 4: JP-A No. 2005-62165
Patent Document 5: International Patent Publication No. WO 2008/047712

SUMMARY OF THE INVENTION

Problems to be Solved by the Invention

Patent Document 5 discloses a manufacturing method including directly cutting an optical film from a material roll into the desired size and bonding the cut piece of the optical film to an optical display unit. Generally in such a method, the material roll of the optical film provided has previously slit into a predetermined width corresponding to the size of the optical display unit. Therefore, the whole of the width of the material roll is bonded to the optical display unit to form the end product, an image display device. Therefore, even if printing is performed on a transverse end part as described in Patent Document 4, the end part will be included in the end product, and therefore, the problem of a dent or any other defect caused by the transfer cannot be overcome.

If the method disclosed in Patent Document 3 is used in which defect information is attached to the material roll without printing on the optical film, the problem of the transfer-induced defect as mentioned above does not occur. In such a case, however, the result of the detection of defects and the position of each defect in the optical film have to be strictly coincident with each other both when positional information about the result of the detection of defects is recorded during the manufacture of the optical film and when the positional information about the result of the detection of defects is read out during the manufacture of an image display device by bonding the optical film to the optical display unit. This not only requires a large amount of labor and cost for the introduction of both systems, the maintenance of the measurement devices, and so on, but also has the risk of causing a problem in which if a mismatch occurs between the record and readout of the positional information about the result of the detection of defects, a non-defective part may be discarded without being bonded to the optical display unit, or a defective part may be bonded to the optical display unit by mistake.

Under the circumstances, it is an object of the invention to provide a material roll that includes a roll of an optical film having defect information markings printed thereon and is resistant to the formation of a defect by the transfer of a bump/dent deformation at the marking site.

Means for Solving the Problems

As a result of investigation, the inventors have completed the invention based on the finding that markings formed with a thickness and an optical density each in a specific range provide high defect-detection accuracy and are less likely to cause the problem of the formation of a dent or any other defect by the transfer even when a material roll is formed by winding an optical film.

The invention relates to a material roll including a long sheet of an optical film having a polarizer, and the optical film is wound into roll shape, wherein at least one marking is formed at or in a vicinity of at least one defect site of the optical film. The marking has an optical density of 1.5 or more, and a thickness of a center part of the marking is 1.5 µm or less. An optical density per unit thickness of the marking is preferably 2.5 $\mu m^{-1}$ or more.

In an embodiment of the invention, the optical film of the material roll has a width that is entirely available for forming a product. In this embodiment, for example, the optical film of the material roll may be bonded to an optical display unit such as a liquid crystal cell in such a manner that the entire width of the optical film is bonded thereto without removal of a transverse end portion of it by slitting or any other process.

Effects of the Invention

According to the invention, the thickness of the marking is the specified value or less, so that the formation of a defect by the transfer of a bump/dent deformation at the marking site is less likely to occur even when an optical film is wound to form a material roll. In addition, the marking site having a specific optical density according to the invention is easy to identify. Therefore, the marking detection rate can be kept high, and the marking site-containing part of the optical film can be removed so as not to be used in combination with other components, which can contribute to cost savings and an increase in the yield of the end product.

EMBODIMENTS FOR CARRYING OUT THE INVENTION

Configuration of Optical Film

Figure 1:
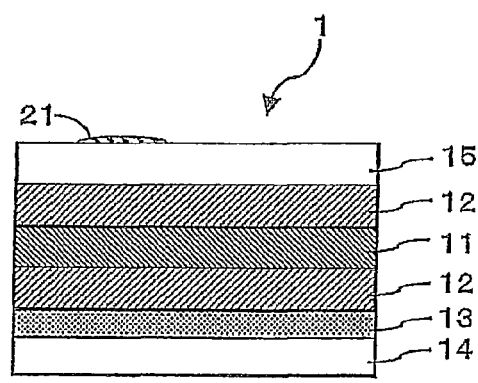
FIG. 1 is a schematic cross-sectional view showing an example of the laminated structure of the optical film.

Hereinafter, preferred embodiments of the invention are described with reference to the drawings as needed. FIG. 1 is a schematic cross-sectional view showing an example of the laminated structure of an optical film 1 used to form a material roll according to an embodiment of the invention. The optical film 1 includes a polarizer 11. The polarizer is intended to include a film capable of converting natural light or polarized light into any type of polarized light. The polarizer for use in an embodiment of the invention preferably converts natural light or polarized light into linearly polarized light, while it may be any appropriate type of polarizer.

Any appropriate type of polarizer may be used depending on the purpose. For example, the polarizer may be a product produced by the steps of adsorbing a dichroic material such as iodine or a dichroic dye to a hydrophilic polymer film such as a polyvinyl alcohol film, a partially-formalized polyvinyl alcohol film, or a partially-saponified ethylene-vinyl acetate copolymer film and uniaxially stretching the film or may be a polyene-based oriented film such as a dehydration product of polyvinyl alcohol or a dehydrochlorination product of polyvinyl chloride. Examples of polarizers that may be used also include an O-type, guest-host polarizer as disclosed in U.S. Pat. No. 5,523,863 in which a liquid crystalline composition containing a dichroic substance and a liquid crystalline compound is oriented in a certain direction, and an E-type polarizer as disclosed in U.S. Pat. No. 6,049,428 in which a lyotropic liquid crystal is oriented in a certain direction. Among such polarizers, a polarizer comprising a polyvinyl alcohol-based film containing iodine is preferably used, because it has a high degree of polarization.

The optical film may also include any other optical layer than the polarizer. For example, such an optical layer may be a transparent film 12a or 12b which is placed as a polarizer protecting film on one or both sides of the polarizer 11. For example, a thermoplastic resin with a high level of transparency, mechanical strength, thermal stability, water blocking properties, isotropy, and other properties is preferably used to form the transparent film 12a or 12b. The polarizer and the transparent film serving as a polarizer protecting film are preferably laminated with an adhesive layer interposed therebetween.

Other Optical Layers

Besides the above, examples of optical layers that may also be used to form the optical film include a hard coat layer, an anti-reflection layer, and a layer having undergone a treatment for anti-sticking, diffusion, or an antiglare purpose, which may be formed on the opposite surface of the transparent film from the polarizer 11. Other examples include a brightness enhancement film, a reflective layer, and a retardation plate (not shown). A polarizer protecting film having the function of serving as a retardation plate may also be preferably used.

A pressure-sensitive adhesive layer 13 may be applied to a main surface of the optical film 1 so that it can be bonded an optical display unit. For example, the pressure-sensitive adhesive to be used to form the pressure-sensitive adhesive layer 13 may be appropriately selected from, but not limited to, pressure-sensitive adhesives containing, as a base polymer, an acrylic polymer, a silicone polymer, polyester, polyurethane, polyamide, polyether, a fluoropolymer, or a rubber polymer. In particular, preferably used is a pressure-sensitive adhesive having a high level of optical transparency, weather resistance and heat resistance and exhibiting an appropriate degree of wettability, cohesiveness and pressure-sensitive adhesive properties, such as an acrylic pressure-sensitive adhesive.

A release film (separator) 13 is preferably temporarily attached with the exposed surface of the pressure-sensitive adhesive layer 13 for antifouling or the like until the optical film is put to practical use. This can prevent contact with the pressure-sensitive adhesive layer during usual handling. According to conventional techniques, appropriate separator 14 may be used such as appropriate thin leaves including plastic films, rubber sheets, paper, cloth, nonwoven fabric, net, foam sheets, metal leafs, and laminates thereof, which are optionally coated with any appropriate release agent such as a silicone, long-chain alkyl or fluoride release agent, or molybdenum sulfide.

Surface Protecting Film

A surface protecting film 15 for protecting the optical film from being scratched or damaged until it is practically used may be temporarily attached to the opposite main surface of the optical film 1 from the surface to which the release film 14 is temporarily attached. The surface protecting film 15 that may be used preferably includes a substrate film made of a plastic film and an easily-peelable, week, pressure-sensitive adhesive layer that is peelably bonded to one surface of the baking film.

The substrate film of the surface protecting film is typically, but not limited to, a biaxially stretched film of polypropylene, polyester or the like. The thickness of the substrate film is preferably, but not limited to, about 10 to about 200 μm.

The pressure-sensitive adhesive used to form the week pressure-sensitive adhesive layer with which the surface protecting film will be temporarily attached to the optical film is typically, but not limited to, any of acryl-based, synthetic rubber-based, and rubber-based pressure-sensitive adhesives. In particular, an acryl-based pressure-sensitive adhesive is preferred, because its adhesive power can be easily controlled by its composition. If necessary, the pressure-sensitive adhesive may also contain a crosslinking agent, a tackifier, a plasticizer, a filler, an antioxidant, an ultraviolet absorbing agent, a silane coupling agent, or any other appropriate additive.

Formation of Markings

The optical film used to form the material roll of the invention has a marking 21 formed at or in the vicinity of a defect site. The term "defect" typically refers to a part that can cause a defect in the display state of an image display device when the optical film is bonded to an optical display unit. The defect may be a part containing foreign matter which should not be present in the optical film under normal conditions, such as a contaminant, bubbles or dirt, or a deformed part such as a dent, a scratch, a concave-convex defect, a curl, or a kink.

For example, such a defect is detected by visual defect inspection or using known defect detection means such as a known defect defection apparatus, and the marking 21 is formed at or in the vicinity of the defect site. The term "defect site" refers to a site whose coordinates in the transverse and longitudinal directions are substantially the same as those of the position of the defect in the optical film. The term "vicinity of the defect site" refers to a region that can be cut together with the defect site into a piece in the process of cutting the optical film into a piece of a predetermined size to be bonded to an optical display unit. The material roll of the invention may be subjected to a manufacturing method including directly feeding the optical film from the material roll, cutting the optical film into a piece of the desired size, and bonding the cut piece of the optical film to an optical display unit. In this case, the difference between the longitudinal coordinates of the defect site and the marking site is preferably within ±200 mm, more preferably within ±100 mm, even more preferably within ±50 mm, in particular, preferably within ±10 mm. On the other hand, the difference between the transverse coordinates is not particularly restricted, and for example, the marking may be formed in a specific position shifted from the defect site in the transverse direction of the film, such as a transverse end.

The marking may be formed on any optical layer of the optical film and may be formed at any stage in the process of manufacturing the optical film. For example, defects in each optical layer may be detected using defect detection means, and markings may be formed on each optical layer, before the layers are laminated into the optical film. Alternatively, the respective optical layers may be laminated into the optical film, and then markings may be formed on the uppermost surface of the optical film.

Defects in the optical film may be detected using defect detection means before the release film or the surface protecting film is temporarily attached to the optical film, and markings may be formed on the release film or the surface protecting film, which may then be temporarily attached. In this case, markings on the release film or the surface protecting film should be formed in positions corresponding to those of the defects in the optical film. The release film or the surface protective film is a process material that is removed in or after the process of bonding of the optical film to an optical display unit and therefore is not contained in an image display device as an end product. Therefore, when defects are detected and markings are formed before the release film or the surface protecting film is temporarily attached, no markings are formed in positions correspond to defects attributable to the process material; so that markings are prevented from being formed even on non-defective portions not responsible for the occurrence of display defects in the formation of an image display device, which can increase the available percentage of the optical film.

When defects in the optical film are detected before the process material such as the release film or the surface protecting film is temporarily attached thereto, markings may be formed on the optical film before the process material is temporarily attached thereto. Markings may also be formed on the process material after the process material is temporarily attached to the optical film which has undergone the defect detection. Alternatively, markings may be formed on the process material in positions corresponding to those of the detected defects at the same time as or after the detection of the defects in the optical film before the temporarily attachment of the process material.

Markings may be formed by any of various known methods such as contact printing methods with such marking means as a pen and non-contact printing methods with such marking means as inkjet. The detection of a defect by defect detection means may be indicated by warning sound or light so that marking can be performed by hand, or appropriate control means may be used to operate marking means in synchronization with defect detection means so that a marking can be automatically formed at or in the vicinity of a defect site. These methods may also be used in combination. In a particularly preferred mode, markings are automatically formed at or in the vicinity of defect sites so that the markings can be formed to have a constant shape or thickness.

In the optical film used to form the material roll of the invention, the center part of the marking 21 has a thickness of 1.5 μm or less. The thickness of the marking may be measured using an optical interference-type surface roughness meter. The "center part of the marking" represents the thickest part of the marking. The "thickness of the center part of the marking" may be determined by dividing the area of a cross-section of the marking by the length of the base (the line intersecting with the surface of the film) of the cross-section, wherein the cross-section passes through the center part of the marking and is perpendicular to the longitudinal direction of the marking. The method for determining the thickness of the marking is described in detail below in the section "EXAMPLES."

If the marking is too thick, the probability of occurrence of a new defect by winding the optical film into a material roll increases. This is because the marking site may be deformed and the deformation may be transferred to another part in contact with the marking site so that a further deformation such as a dent may occur when the optical film is wound into a material roll. From this point of view, the thickness of the marking is preferably 1.2 μm or less, more preferably 1.0 μm or less, in particular, preferably 0.8 μm or less.

To prevent a defect from occurring due to transfer of deformation of the marking site, a thickness of the center part of the marking is preferably as small as possible. However, if the marking is too thin, the optical density described below may be so low that the marking detection rate of the marking detection means may tend to be reduced. From this point of view, the thickness of the marking is preferably 0.3 μm or more, more preferably 0.5 μm or more.

The thickness of the marking can be controlled by the type of the marking means for forming the marking, such as a pen or inkjet, the contact pressure (writing pressure) between a pen as the marking means and the optical film, the size of ink droplets ejected from an inkjet nozzle as the marking means, the concentration of the ink, or any other factor. When the marking is formed on the film being fed, the thickness of the marking can also be controlled by changing the film feeding speed.

In the optical film used to form the material roll of the invention, the marking preferably has an optical density of 1.5 or more. The term "optical density" refers to the absorbance of the marking at an absorption peak wavelength, which may be determined by measuring the absorption spectrum of the marking site with a micro-spectrophotometer. Therefore, "high optical density" means that the marking site has a high absorbance at the absorption peak wavelength, and as the optical density increases, the marking detection rate of the marking detection means tends to increase. The marking detection rate should be prevented from being reduced in the marking detection step performed at an increased film feeding speed. From this point of view, the marking preferably has an optical density of 2.0 or more, more preferably 2.5 or more, even more preferably 3.0 or more, in particular, preferably 3.5 or more. A method for measuring the optical density is described in detail below in the section "EXAMPLES."

The optical density per unit thickness of the marking is obtained by dividing the optical density by the thickness of the marking. In a preferred mode, the optical density should be set high, while the thickness of the marking should be the specified value or less, and the optical density per unit thickness of the marking should be set high to increase the marking detection rate. The optical density per unit thickness of the marking is preferably 2.5 $\mu m^{-1}$ or more, more preferably 2.8 $\mu m^{-1}$ or more, even more preferably 3.0 $\mu m^{-1}$ or more, in particular, preferably 3.2 $\mu m^{-1}$ or more. Appropriate marking means is preferably used so that the optical density per unit thickness of the marking can be increased. Various types of ink may be used for such marking means, and in particular, ink with a high absorption coefficient is preferably used. For example, such ink with a high absorption coefficient preferably shows an absorption spectrum with a sharp absorption peak and with a narrow spectral band width (half-value width).

Such absorption characteristics may be evaluated by any appropriate means. For example, when a commercially available pen is used as the marking means, lines may be drawn on a transparent film using the pen, and the absorption spectrum of the drawing may be measured, so that the absorption characteristics can be evaluated. The absorption characteristics may be previously evaluated in such a manner, before markings are formed on an optical film as a real product, so that markings with the desired optical density can be formed without undue trials and errors.

As described above, the material roll of the invention is characterized in that a relatively thin marking is formed on the optical film so that a defect such as a dent can be prevented from occurring due to the transfer by winding the optical film into the material roll and that the marking has a relatively high optical density per unit thickness so that marking detection means can have a high detection rate, in other words, detection missing can be reduced.

The absorption wavelength range or absorption peak wavelength of the marking is not particularly restricted as long as it can be detected by the marking detection means, and it may be not only in the visible light range (380 nm to 780 nm) but also in the ultraviolet light range or the infrared light range. For example, when the optical film includes a polarizer, the detection of the marking on the optical film tends to be less easy than the detection of the marking on a transparent film, because the polarizer absorbs light in the visible range. Therefore, the marking should have an absorption peak at a wavelength in a region where the absorbance of the polarizer is low, so that high marking-detection sensitivity can be obtained.

On the other hand, when a widely-used silicon-based detector is used in the marking detection means, the marking preferably has an absorption peak at a wavelength in the visible light range. To be visually identified, the marking also preferably has an absorption peak at a wavelength in the visible light range. Particularly to have high visibility, the marking preferably has an absorption peak at a wavelength in the range of 500 nm to 600 nm. The range of 500 nm to 600 nm corresponds to a blue green-green-yellow-orange spectrum area. Therefore, when the absorption is in this wavelength range, the transmitted or reflected light shows the complementary color, red-violet-blue. If the amount of light in the wavelength range of 500 to 600 nm is relatively large, it may be difficult to visually identify the difference between the marking and the non-absorptive part around the marking, because the human vision is most sensitive to yellow-yellow green. However, when the absorption peak is in the above wavelength range, the marking is easy to visually identify even with the absorbance (specifically, the optical density) being relatively low.

Formation of Material Roll

The optical film on which the markings are formed as described above is wound into the material roll. More specifically, the material roll may be produced by winding a sheet material under a specific tension around a core with a specific diameter.

The outer diameter of the core is generally 70 mm or more, more preferably 150 mm or more. If the outer diameter of the core is too small, there may be a problem in which the release film or the surface protecting film temporarily attached to the optical film may peel off due to a large curvature near the core. On the other hand, the outer diameter of the material roll obtained after the winding has an upper limit. Therefore, if the outer diameter of the core is too large, a length of sheet material wound around the core has to be relatively small. From these points of view, the outer diameter of the core is preferably selected so that a material roll with an outer diameter (roll diameter) of 1,500 mm or less, more preferably 1,000 mm or less can be obtained by winding the optical film.

The tension (winding tension) applied to the optical film in the process of winding it around the core is preferably 50 N/m or more, more preferably 100 N/m or more. If the tension is too low, the winding may not be successfully performed. If the winding tension is too high, the bump/dent shape of the marking may be transferred to a part in contact with the marking site during the winding process, so that a deformation such as a dent may tend to often occur. Therefore, the winding tension is preferably 300 N/m or less, more preferably 200 N/m or less.

The material roll of the invention also preferably has a width corresponding to the size of the end product. The end product is typically an image display device such as a liquid crystal display, which is formed by a process including feeding the optical film from the material roll and bonding the optical film to an image display unit such as a liquid crystal cell. In general, a material roll with a width larger than the size of the optical display unit is obtained. Therefore, such a material roll is slit into a predetermined size corresponding to the size of the optical display unit so that a width corresponding to the size of the end product can be obtained. Such slitting into a predetermined size may be performed in the process of manufacturing the optical film so that a slit material roll with the predetermined size can be obtained. Alternatively, a slit material roll of a predetermined size may also be obtained by a process including temporarily winding a wide optical film into a material roll, then feeding the optical film from the wide material roll, slitting the optical film into a predetermined size, and then winding the resulting strip around a core.

The material roll of the invention is preferably used in forming an image display device such as a liquid crystal display, an organic electroluminescence (EL) display, or a plasma display panel (PDP). The image display device may be formed according to conventional techniques. For example, a liquid crystal display as the image display device may be formed by a process including assembling a liquid crystal cell (corresponding to the optical display unit) and optical films and optional components such as a lighting system, and building a driving circuit thereinto. The liquid crystal cell to be used may be of any type such as twisted nematic (TN) type, super twisted nematic (STN) type, or π type. In the process of forming the liquid crystal display, an additional appropriate component such as a prism array sheet, a lens array sheet, a light diffusion plate, or a backlight may also be placed at an appropriate location.

Manufacturing of Image Display Device

The material roll of the invention has a marking at or in the vicinity of a defect site. Therefore, the image display device is preferably manufactured by a method including bonding only a marking-free part of the optical film to an optical display unit.

In particular, the image display device should be manufactured at a reduced cost and with an improved yield. In this point of view, a marking detection step including feeding a long sheet material of the optical film from the material roll and detecting the presence or absence of a marking by inspection means capable of identifying it, a cutting step including transversely cutting the optical film, by cutting means, into a size suitable for bonding the optical film to the substrate of an optical display unit, and a bonding step including bonding the suitable size cut piece of the optical film to the substrate of the optical display unit are preferably performed as a series of continuous steps.

In the manufacturing method including such continuous steps, the cutting step may be performed in such a manner as to remove, from the product, the marking-containing part detected in the marking detection step, or the detected marking-containing part may be bonded to a part other than the substrate of the optical display unit so that only the marking-free part can be bonded to the optical display unit.

Figure 2:
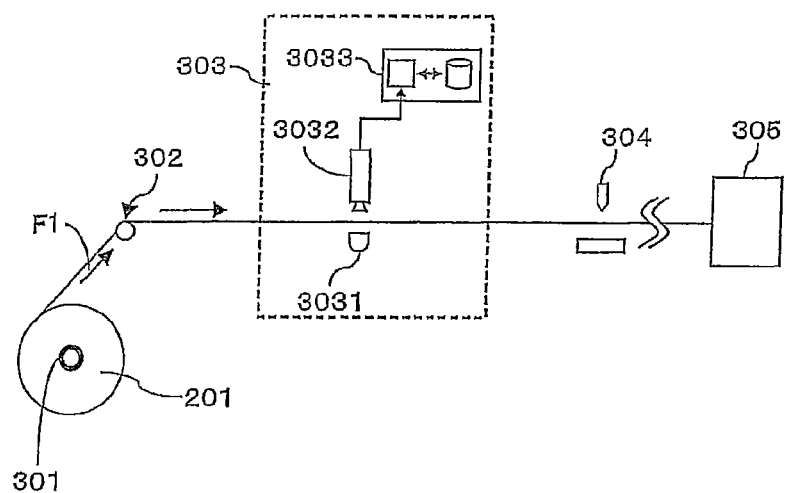
FIG. 2 is a schematic diagram for illustrating an image display device manufacturing process according to an embodiment of the invention.

FIG. 2 is a schematic diagram showing an example of the process of manufacturing an image display device according to the invention. Each step of the process is described below with reference to the drawing.

(1) Marking Detection Step

A material roll 201 of the optical film having markings formed thereon is mounted on a roll mount apparatus 301 that is geared to a motor or the like to rotate freely or at a certain speed. A sheet material F1 of the optical film is fed from the roll 201 and to the downstream side. The feeder to be used preferably includes a number of feed rollers 302 and is configured to feed the sheet material F1 along a feed path formed with the feed rollers. The feed path extends from the material roll feeding site to the site where the material is bonded to the optical display unit.

The presence or absence of the marking in the sheet material F1 of the optical film being fed is detected by marking detection means 303. The marking is preferably detected using a method in which the presence or absence of the marking can be identified by a reduction in the intensity of transmitted or reflected light produced at the marking site by the application of light to the sheet material.

FIG. 2 shows marking detection means 303 that applies light to the sheet material F1 and detects the intensity of the resulting transmitted light so that it can detect the marking. In the illustrated example, the marking detection means 303 includes a light source 3031, a camera 3032, and a camera controller 3033. Light from the light source 3031 is applied to the sheet material F1, and the resulting transmitted light enters the camera 3032. The camera 3032 is an optical device such as a CCD camera, which has an appropriate lens and can detect the intensity of the incident light at each position (pixel). The information about the intensity of the incident light detected at each pixel of the camera is sent to the camera controller 3033. The intensity of the incident light detected by the camera is converted by the camera controller 3033 to a signal representing a specific tone (for example, 8 bits (black and white)=256 tones).

Since the optical film has a specific optical density at the marking site, the intensity of the transmitted light through the marking site is lower than that through the part around it, when light is applied from the light source 3031. Therefore, the marking site and the part around it are different in the tone for the intensity of the transmitted light. The camera controller 3033 calculates the difference (Y−X) between the tone (X) for the low intensity of the transmitted light through the site and the tone (Y) for the intensity of the transmitted light through the part around it, and determines that the low-transmitted-light-intensity site has "the marking," when Y−X is larger than the predetermined threshold value. On the other hand, when Y−X is smaller than the threshold value, it is determined that the lower intensity of the transmitted light through the site than that through the part around it is due to a noise and that the site has "no marking." If the threshold value is set too high, the marking detection rate will tend to be low, and if the threshold value is set too low, noise-induced false detection (over-detection) will tend to increase. Therefore, the threshold should preferably be set to an appropriate value depending on the characteristics such as the spectral characteristics or the characteristics of the camera.

The camera controller 3033 also calculates the coordinates of the position of the site determined to "have the marking." It should be noted that it is enough to calculate only the coordinate of the position in the feed direction of the sheet material. The data on the coordinate(s) of the position of the marking is sent to a skip cutting or removal mechanism for the cutting step described below, so that only a marking-free part can be bonded to an optical display unit to form an image display device.

When the material roll of the invention is used, the marking detection step can be performed at a high marking-detection rate, in other words, with a low probability of missing the detection of the marking, because the marking site in the optical film has the specified optical density. Therefore, the marking-containing part of the optical film can be prevented from being bonded to an optical display unit.

(2) Cutting Step

After the presence or absence of the marking is determined by the marking detection step, the sheet material F1 is cut into a predetermined size corresponding to the size of the optical display unit by cutting means 304 in the cutting step. For example, the cutting means 304 may be a laser, a cutter, or any other known cutting means. If the material roll 201 has previously undergone slitting into a predetermined width corresponding to the size of the optical display unit, specifically, slitting into a length corresponding to the long or short side of the optical display unit, the sheet material can be cut into a predetermined size corresponding to the size of the optical display unit only by cutting it at predetermined intervals in the feed direction (the longitudinal direction of the sheet material) in the cutting step.

[Full Cutting Method]

The cutting step may be performed using a method in which all the optical layers of the optical film are completely cut (full cutting). The full cutting method may include holding the fed sheet material F1 by appropriate holding means (not shown) such as a suction device and cutting all the components of the optical film by the cutting means 304 along the transverse direction parallel to the core of the material roll. The cut piece of the sheet material is fed to bonding means 305, while it is held by the holding means.

[Half Cutting Method]

Alternatively, at least one of the optical layers may be left uncut (half cutting). A description is given of an example of such a half-cutting mode in which as shown in FIG. 1, the optical film 1 has a configuration including a polarizer 11, transparent films 12*a* and 12*b* placed on both sides of the polarizer 11, a surface protecting film 15 placed on one of the films 12*a* and 12*b*, and a pressure-sensitive adhesive layer 13 and a release film 14 placed on the other of the films 12*a* and 12*b*. The cutting means 304 cuts the surface protecting film 15, the polarizer 11, the transparent films 12*a* and 12*b* placed on both sides thereof, and the pressure-sensitive adhesive layer 13 along the transverse direction parallel to the core of the material roll, without cutting the release film 14. In this way, the release film, which is a process material not to be bonded to the optical display unit, is left uncut, so that the feed tension is transmitted from the feeder to the cut piece of the sheet material through the release film 14. Even after the cutting, therefore, the sheet material can be transported to bonding means 305 under the feed tension.

[Skip Cutting Method]

The cutting step may also be performed in such a manner that the marking-containing part detected in the marking detection step is removed from the product. In this case, the marking position coordinate information obtained by the marking detection step is sent to the cutting step, and based on the coordinate information, the cutting step is performed so as to avoid the marking site (skip cutting). Specifically, the cut piece containing the defect is removed as defective by a removal mechanism in a later step. This can significantly increase the available percentage of the optical film. The marking-containing part of the sheet material F1 is removed by the removal mechanism (not shown) so as not to be bonded to the optical display unit W.

Alternatively, the presence of the marking may be ignored, and the sheet material F1 may be continuously cut into pieces of a predetermined size without performing the skip cutting. In this case, the bonding step described below is preferably performed in such a manner that the corresponding part is not bonded to the optical display unit W but removed.

(3) Bonding Step

The predetermined-size cut piece of the sheet material F1 obtained in the cutting step is bonded by bonding means 305 to the optical display unit with the pressure-sensitive adhesive layer interposed therebetween. When the release film is temporarily attached to the sheet material F1, the bonding is performed after or while the release film is removed. When the full cutting method is used in the cutting step, the release film may be removed by a process including feeding a pressure-sensitive adhesive tape from a roll thereof, attaching the pressure-sensitive adhesive tape to the release film while pressing it with a roll, and winding the pressure-sensitive adhesive tape so as to peel off the release film. When the half-cutting method is used in the cutting step, the release film may be removed by a method including peeling off the release film, while winding the optical layer (for example, the release film) left uncut into a roll by appropriate winding means. The release film may be peeled off by hand or using a known release film peeling apparatus. For example, the sheet material F1 may be preferably bonded to the optical display unit using a method that includes bonding the sheet material F1 to the surface of the optical display unit, while pressing the sheet material F1 against the surface of the optical display unit using one or more press rollers, guide rollers, or other rollers.

For example, the marking-containing part of the sheet material may be bonded to an alternative plate unit (not shown) or wound around an appropriate roller so that it can be removed without being bonded to the optical display unit. When the half-cutting method is used, the optical layer (for example, the release film) left uncut and being attached may also be wound by winding means.

The use of the above steps eliminates the need for handling the optical film in the form of a cut piece of a specific size and therefore can increase production efficiency. Also when the above steps are used, cutting a polarizing plate into a specific length and bonding the cut piece to an optical display unit, which are separately performed by an optical film manufacturer and a panel processing manufacturer in a conventional image display manufacturing method, can be continuously performed in a single place, so that end face working, clean packaging, or packaging for transportation, which has been performed on a polarizing plate by an optical film manufacturer, or unpacking, which has been performed by a panel processing manufacturer, will be unnecessary, which can contribute to cost savings and an increase in yield.

EXAMPLES

The invention is further described by the examples below, which are not intended to limit the scope of the invention.

Optical Film

The material roll used was a roll of an optical film ("NPF VEG1724DU" (trade name) manufactured by NITTO DENKO CORPORATION) including: a polarizing plate including a polarizer of an iodine-dyed, polyvinyl alcohol-based film and transparent films placed as polarizer protecting films on both sides of the polarizer; an acryl-based, pressure-sensitive adhesive layer provided on the surface of one of the polarizer protecting films; and a separator of a silicone release agent-coated polyethylene terephthalate film temporarily attached to the pressure-sensitive adhesive layer.

Formation of Markings

Figure 3:
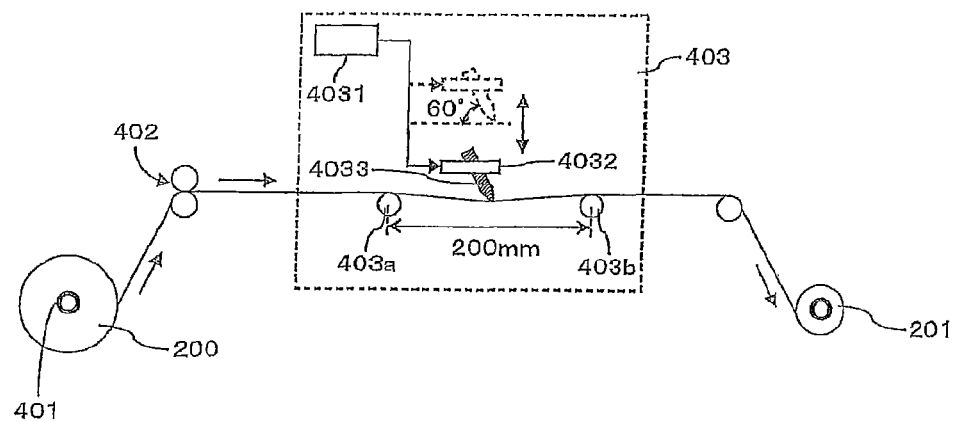
FIG. 3 is a schematic diagram for illustrating a marking method and the configuration of marking means used in the EXAMPLEs.

Using marking means 403 as shown in FIG. 3, a 20 mm long marking was formed on the surface of the polarizer protecting film on the side of the optical film where the pressure-sensitive adhesive layer was not provided. As shown in FIG. 3, the optical film having no marking is fed from the material roll 401 at a feed rate of 10 m/minute using a pair of nip driving rolls 402 and guided in such a manner that the pressure-sensitive adhesive layer side of the optical film runs on support rolls 403a and 403b placed 200 mm apart from each other. The marking means 403 has an actuator 4031 driven by a servo motor, and a pen 4033 is placed in a holder 4032 at the top of the actuator 4031. When the actuator operates, the pen 4033 moves vertically. When marking is performed, the pen 4033 moves downward so that the tip of the pen comes into contact with the surface of the protecting film of the optical film at an angle of 60° from 5 mm above the surface.

Comparative Example 1

An oil-based black permanent marker pen ("V Super Color" (trade name) manufactured by PILOT Corporation) was used as the pen 4033 in the marking means shown in FIG. 3, and a 5 mm wide, 20 mm long marking was formed, which was called "marking A."

Comparative Example 2

An oil-based black permanent marker pen (Jun-Shin (trade name) manufactured by Shachihata Inc.) was used as the pen 4033 in the marking means shown in FIG. 3, and a 5 mm wide, 20 mm long marking was formed, which was called "marking B."

Comparative Example 3

An oil-based black permanent marker pen (Jun-Shin (trade name) manufactured by Shachihata Inc.) was used as the pen 4033 in the marking means shown in FIG. 3, and a 5 mm wide, 20 mm long marking was formed. In COMPARATIVE Example 3, the uncapped pen was allowed to stand at room temperature (22° C.) for 48 hours and then used. The marking was called "marking C."

Example 1

An oil-based black permanent marker pen ("Lumocolor" (trade name) manufactured by STAEDTLER) was used as the pen 4033 in the marking means shown in FIG. 3, and a 5 mm wide, 20 mm long marking was formed, which was called "marking D."

Measurement of the Thickness of the Marking

The separator was peeled off from the optical film having the marking formed thereon according to each of the EXAMPLE and the COMPARATIVE EXAMPLEs. Using a hand roller, the optical film was then bonded to a 50 mm×100 mm slide glass (manufactured by Matsunami Glass Ind, Ltd.) with the acryl-based pressure-sensitive adhesive layer (which was previously provided on the optical film) interposed therebetween. The resulting surface profile was measured using an optical interference-type surface roughness meter ("WYKO NO800" (trade name) manufactured by Vecco Instruments Inc.) under the following conditions: base line set on the meter side surface of the optical film; back scan, 30 μm; scan length, 40 μm; modulation threshold, 0.1%; stitching, X=25 mm, Y=8 mm.

The resulting surface profile data was used to determine the area of a cross-section passing through the lengthwise midpoint of the marking and being perpendicular to the longitudinal direction of the marking. The thickness of the center part of the marking was determined by dividing the cross-sectional area by the base of the cross-section.

Measurement of Optical Density

Each optical film having the marking formed thereon according to each of the EXAMPLE and the COMPARATIVE EXAMPLEs was bonded to a 50 mm×100 mm slide glass (manufactured by Matsunami Glass Ind, Ltd.) using a masking tape ("No. 7235" manufactured by NITTO DENKO CORPORATION). The absorption spectrum of a very small region at the center part of the marking was measured using a micro-spectrophotometer ("LV Micro" (product name) manufactured by Lambda Vision inc.) under the conditions below, and the optical density was defined as the peak value of the absorbance.

Light source: halogen-deuterium light source
Pinhole size: 100 μmφ
Sensor: Multidetector
Measurement mode: transmittance measurement mode.

Table 1 shows the thickness of the center part of the marking, the optical density, and the optical density per unit thickness (obtained by dividing the optical density by the thickness of the center part of the marking) with respect to the optical film obtained in each of the EXAMPLE and the COMPARATIVE EXAMPLEs.

TABLE 1

|  | Marking thickness (μm) | Optical density | Optical density per unit thickness (μm$^{-1}$) |
|---|---|---|---|
| COMPARATIVE EXAMPLE 1 | 2.1 | 7.6 | 3.6 |
| COMPARATIVE EXAMPLE 2 | 1.6 | 3.0 | 1.9 |
| COMPARATIVE EXAMPLE 3 | 0.8 | 1.4 | 1.8 |
| EXAMPLE 1 | 0.7 | 2.5 | 3.5 |

Evaluation of Load in Material Roll

The load on an optical film in a material roll of the optical film was evaluated. The same raw long optical film ("NPF VEG1724DU" (trade name) manufactured by NITTO DENKO CORPORATION, about 1,000 m in length) as used in the EXAMPLE and the COMPARATIVE EXAMPLEs was fed in the longitudinal direction under a tension of 200 N/m and wound around a core with an outer diameter of 152 mm. In the winding process, PRESCALE (ultra-low pressure type (0.5 to 2.5 MPa) manufactured by FUJIFILM Corporation) with a size of 50 mm×100 mm was inserted at about 10 m, about 300 m, about 600 m, and about 900 m from the winding start. After the material roll was formed, the change in the hue of PRESCALE was evaluated using a specialized scanner ("FPD9210" (product name) manufactured by FUJIFILM Corporation), so that the load on PRESCALE was determined. Table 2 shows the relationship between the load and the point from the film winding start.

TABLE 2

| Wound length (m) | Load (Mpa) |
|---|---|
| 10 | 2.5 |
| 300 | 1.7 |
| 600 | 1.1 |
| 900 | 0.4 |

The result indicates that in a material roll of an about 1,000 m long sheet, the frequency of defects such as dents formed by the transfer of markings is required to be low still when a load of 3 MPa is applied to a part close to the core.

Evaluation of Frequency of Dents

Figure 4:
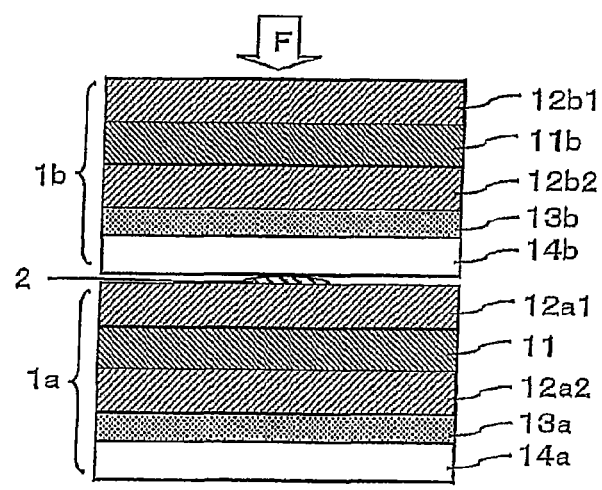
FIG. 4 is a schematic cross-sectional view for illustrating the laminated structure of an optical film used for the evaluation of the frequency of dents in the EXAMPLEs.

As shown in FIG. 4, an optical film 1b having no marking was superposed on an optical film 1a including a transparent film 12a1 and a marking formed thereon, and they were allowed to stand at room temperature for 48 hours, while a weight was placed thereon to apply a specific load F thereto from the optical film 1b side. Subsequently, the surface of the release film 14b of the optical film 1b, which had been in contact with the marking 21, was visually observed, and the presence or absence of a dent defect was determined. Optical films having markings A to D, respectively, were prepared as in the EXAMPLE and the COMPARATIVE EXAMPLEs, and ten samples of each of the optical films were determined for the presence or absence of a dent defect at each of four load levels 0.5 MPa, 1.0 MPa, 2.0 MPa, and 3.0 MPa, so that the frequency of dents formed by the loading was evaluated. The results are shown in Table 3.

TABLE 3

| | Load (MPa) | | | |
|---|---|---|---|---|
| | 0.5 | 1.0 | 2.0 | 3.0 |
| COMPARATIVE EXAMPLE 1 | 50% | 90% | 100% | 100% |
| COMPARATIVE EXAMPLE 2 | 10% | 30% | 40% | 60% |
| COMPARATIVE EXAMPLE 3 | 0% | 0% | 0% | 10% |
| EXAMPLE 1 | 0% | 0% | 0% | 10% |

Evaluation of Marking Detection Rate

<Material Roll>

The material roll used was a material roll each having 20 markings A, B, C or D previously printed on random parts of the surface of the polarizer protecting film on the side of the polarizing plate where the pressure-sensitive adhesive layer was not provided. Each material roll has the same laminated structure as used in the EXAMPLE and the COMPARATIVE EXAMPLEs and including a 400 mm wide, about 200 m long optical film ("NPF VEG1724DU" (trade name) manufactured by NITTO DENKO CORPORATION).

<Marking Detection Apparatus>

Figure 5:
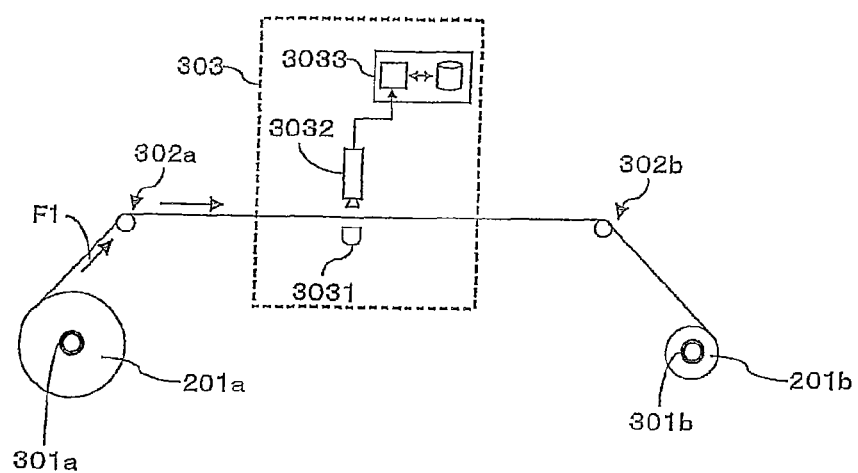
FIG. 5 is a schematic diagram for illustrating the configuration of a marking detection evaluation apparatus used for the evaluation of the marking detection rate in the EXAMPLEs.

FIG. 5 schematically shows the configuration of an apparatus for evaluating marking detection, which was used in the evaluation of marking detection. The material roll is mounted on a first roll mount 301a, and the sheet material F1 is allowed to run between the first roll mount 301a and a second roll mount 302a. Marking detection means 303 is provided at some midpoint in the feed path so as to detect the markings. In the marking detection means 303, light is applied from a light source 3031 ("FL48/800W85-DF" (product name) manufactured by Raytronics Corp.) to the sheet material F1, and the resulting transmitted light enters a camera 3032 ("CV-2000M" (product name) manufactured by KEYENCE CORPORATION) through a lens ("CA-LH8" (product name) manufactured by KEYENCE CORPORATION). The information about the intensity of the incident light detected by the camera is sent to a camera controller 3033 ("CV-2000" (product name) manufactured by KEYENCE CORPORATION). The camera controller converts the intensity of the incident light (detected by the camera) to 256 black-and-white tones. The camera controller calculates the difference Y–X between the tone X at the low transmitted-light intensity site and the tone Y at the part around the site, and determines that the low transmitted-light intensity site "has a marking," when Y–X is greater than the pre-set threshold value (100).

Evaluation of Marking Detection

The sheet material F1 from the material roll 201a was fed from the first roll mount 301a side to the second roll mount 301b side at a feed rate of 1.0 m/minute, and the markings were detected by the marking detection means during the feeding. After the optical film was entirely taken up onto the second roll mount 302a, the optical film was in turn fed from the second roll mount 301b side to the first roll mount 301a side at a feed rate of 3.0 m/minute, and the markings were detected by the marking detection means during the feeding. Thereafter, the feeding rate was changed to 5.0 m/minute and to 10.0 m/minute, and the detection was evaluated in the same manner. The marking detection rate at each feed rate is shown in Table 4.

TABLE 4

| | Feed rate (m/minute) | | | |
|---|---|---|---|---|
| | 1.0 | 3.0 | 5.0 | 10.0 |
| COMPARATIVE EXAMPLE 1 | 100% | 100% | 100% | 100% |
| COMPARATIVE EXAMPLE 2 | 100% | 100% | 100% | 100% |
| COMPARATIVE EXAMPLE 3 | 100% | 95% | 90% | 70% |
| EXAMPLE 1 | 100% | 100% | 100% | 100% |

The following is apparent from the EXAMPLE and the COMPARATIVE EXAMPLEs. When the marking is relatively thick as in COMPARATIVE EXAMPLE 1 or 2, the frequency of dents formed by the transfer of the marking tends to increase as a relatively high load is applied to the optical film in the vicinity of the core of the material roll. When the marking is relatively thin, the frequency of dents is relatively low, but the marking detection rate tends to be low as in COMPARATIVE EXAMPLE 3, because the optical density is relatively low. In contrast, the optical film obtained in EXAMPLE 1, where the marking has a relatively high optical density, shows a marking detection rate as high as that in COMPARATIVE EXAMPLE 2 where the marking is relatively thick, although the marking is thinner in EXAMPLE 1 than in COMPARATIVE EXAMPLE 1.

DESCRIPTION OF REFERENCE CHARACTERS 1 an optical film,
11 a polarizer,
12a a transparent film,
12b a transparent film,
13 a pressure-sensitive adhesive layer,
14 a release film,
15 a surface protecting film,
21 a marking,
201 a material roll,
301 a roll mount,
302 a feed roller,
303 marking detection means,
304 cutting means,
305 bonding means,
3031 a light source,
3032 a camera,
3033 a camera controller,
F1 a sheet material,
W an optical display unit.

The invention claimed is:

1. A material roll, comprising:
a long sheet of an optical film wound into roll shape, the optical film comprising a polarizer, wherein
at least one marking is formed at or in a vicinity of at least one defect site of the optical film,
the marking has an optical density of 1.5 or more, and
a thickness of a center part of the marking is 1.5 μm or less;
wherein the marking is formed of ink from an inkjet printer or the marking is formed of ink from a pen, and
wherein the marking has an optical density per unit thickness of 2.5 $\mu m^{-1}$ or more.

2. The material roll according to claim 1, wherein the optical film has a width that is entirely available for forming a product.

3. The material roll according to claim 1, wherein the marking has an absorption peak at a wavelength of 500 nm to 600 nm.

* * * * *